(12) United States Patent
Chen

(10) Patent No.: US 8,774,935 B2
(45) Date of Patent: Jul. 8, 2014

(54) DISASSEMBLABLE FAR INFRARED KNEE-AND-FOOT WARMING DEVICE

(75) Inventor: Ching-Song Chen, Taichung (TW)

(73) Assignee: Dian Chiang Chia Technology Co., Ltd., Taichung Industry Park, Taichung (TW)

( * ) Notice: Subject to any disclaimer, the term of this patent is extended or adjusted under 35 U.S.C. 154(b) by 938 days.

(21) Appl. No.: 12/925,020

(22) Filed: Oct. 12, 2010

(65) Prior Publication Data

US 2012/0085335 A1  Apr. 12, 2012

(51) Int. Cl.
*A61F 2/00*  (2006.01)
*A61F 7/00*  (2006.01)

(52) U.S. Cl.
USPC .......................................... 607/100; 607/111

(58) Field of Classification Search
USPC .................................................. 607/96, 100
See application file for complete search history.

(56) References Cited

U.S. PATENT DOCUMENTS

| 4,495,935 | A | * | 1/1985 | Lanier | 126/204 |
| 6,004,344 | A | * | 12/1999 | Fujii | 607/91 |
| 6,276,001 | B1 | * | 8/2001 | Chen | 4/527 |
| D529,619 | S | * | 10/2006 | Onozawa | D24/212 |
| 2002/0183814 | A1 | * | 12/2002 | Ono | 607/100 |
| 2006/0136020 | A1 | * | 6/2006 | Dussault | 607/96 |

FOREIGN PATENT DOCUMENTS

| EP | 1847784 A1 | * | 10/2007 | F24H 3/00 |
| GB | 2461806 A | * | 1/2010 | A61N 5/06 |

\* cited by examiner

*Primary Examiner* — Linda Dvorak
*Assistant Examiner* — Adam Avigan
(74) *Attorney, Agent, or Firm* — Charles E. Baxley

(57) ABSTRACT

A disassemblable far infrared knee-and-foot warming device includes a bottom plate, a top plate, a front frame, a curved plate, a plurality of screws and an opening. By operating the screws, the bottom plate, the top plate, the front frame and the curved plate can be assembled or disassembled, and the curved plate is provided with a far infrared heating plate. Thereby, the far infrared heating plate generates far infrared thermal energy, and the warming device can be easily disassembled for saving costs related to packaging, storage and transportation, and can be easily reassembled for use.

4 Claims, 6 Drawing Sheets

DISASSEMBLABLE FAR INFRARED KNEE-AND-FOOT WARMING DEVICE

BACKGROUND OF THE INVENTION

1. Technical Field

The present invention is related to health care equipment, and more particularly, to a disassemblable far infrared knee-and-foot warming device.

2. Description of Related Art

Referring to FIG. 1, an existing knee-and-foot warming device has a housing primarily constructed from a plurality of wood planks 101, a top plate 102 and a bottom plate 103. For assembling the housing, the wood planks 101 are vertically and/or horizontally set abreast to form a hollow column and fixedly adhered to each other before adhesively assembled with the top plate 102 and the bottom plate 103.

While being useful to meet the purpose it is made for, the conventional knee-and-foot warming device nevertheless has the following defects:

1. Since the top plate 102, the bottom plate 103 and the wood planks 101 are fixedly bound together by adhesive, the resultant knee-and-foot warming device is not disassemblable after manufactured.

2. The resultant knee-and-foot warming device is bulky and not reducible, so it takes considerable space for its packaging, transportation and storage, which is inconvenient and uneconomic.

3. Even putting the issue about limited forest resources aside, the wood planks 101, after long-term use in changeable environmental conditions, are likely to perform deformation, which adversely affects the tight combination therebetween and is in turn unfavorable to the overall thermal efficiency of the knee-and-foot warming device. Moreover, wood is in nature vulnerable under impact and attrition that may frequently happen in transportation and use of the device, so the intact appearance of the device is hardly maintainable.

SUMMARY OF THE INVENTION

In view of the defects of the existing device as described above, the primary objective of the present invention is to provide a disassemblable far infrared knee-and-foot warming device that can be easily disassembled for saving costs related to packaging, storage and transportation, and can be easily reassembled for use.

Thus, the disassemblable far infrared knee-and-foot warming device of the present invention comprises a bottom plate, a top plate, a front frame, a curved plate, a plurality of screws and an opening. The bottom plate has an upper surface which is formed with a lower retaining groove extending along an outline of the bottom plate. The top plate has a lower surface facing the upper surface, wherein the lower surface is formed with an upper retaining groove extending along an outline of the top plate. The front frame is connected between the bottom plate and the top plate and having two vertically extending ruts. The curved plate has a far infrared heating plate, a thermal insulation layer covering the far infrared heating plate, a pattern layer covering the thermal insulation layer, a bottom edge to be received in the lower retaining groove, a top edge to be received in the upper retaining groove, and two opposite lateral edges to be received in the ruts, wherein the far infrared heating plate has two insulation layers and a heating layer sandwiched between the insulation layers. The screws serve to fasten the bottom plate, the top plate and the front frame together. The opening is provided on any one of the top plate and the front frame.

By operating the screws, the bottom plate, the top plate, the front frame and the curved plate can be assembled or disassembled. Thereby, the warming device can be easily disassembled for saving costs related to packaging, storage and transportation, and can be easily reassembled for use.

BRIEF DESCRIPTION OF THE DRAWINGS

The invention as well as a preferred mode of use, further objectives and advantages thereof will be best understood by reference to the following detailed description of an illustrative embodiment when read in conjunction with the accompanying drawings, wherein.

DETAILED DESCRIPTION OF THE INVENTION

Figure 1:
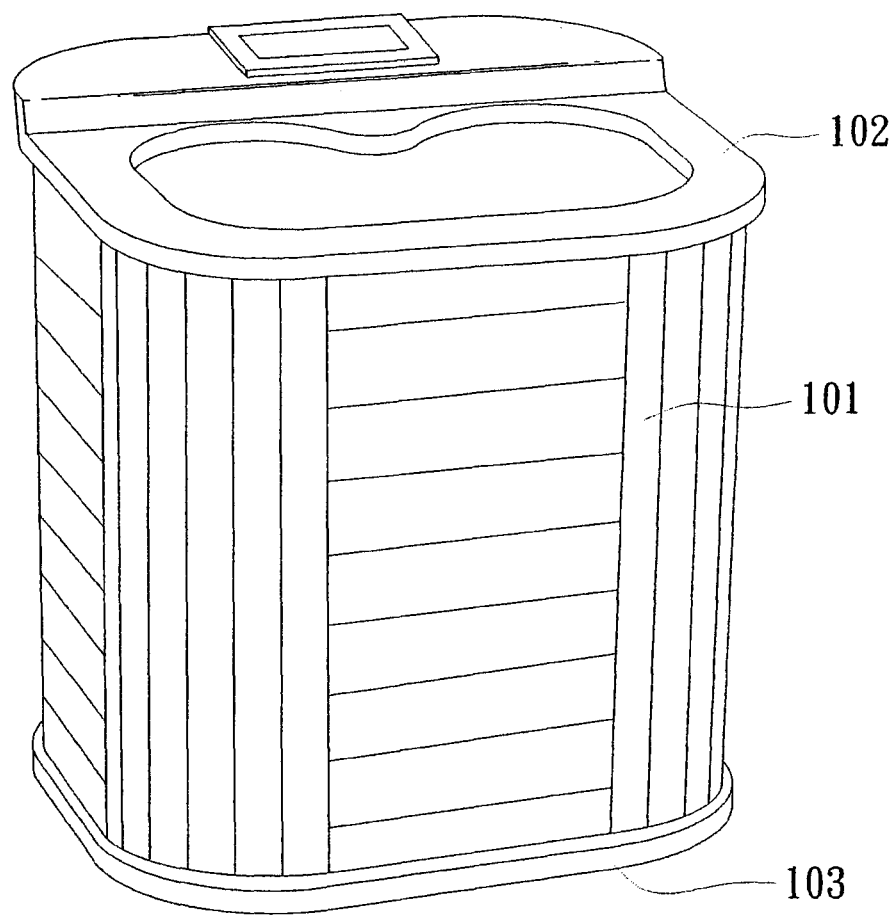
FIG. 1 is a perspective view of an existing knee-and-foot warming device.
Figure 2:
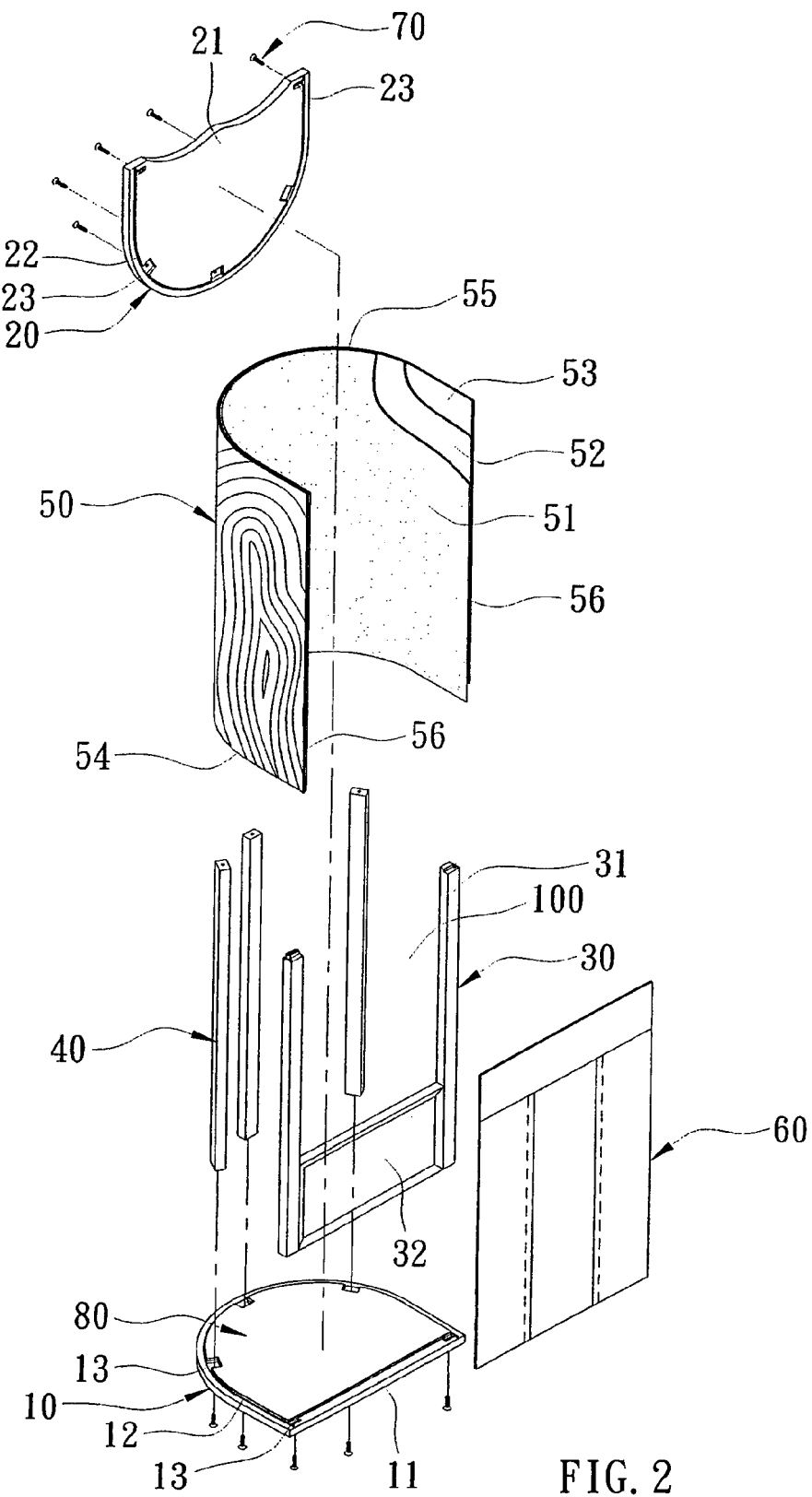
FIG. 2 is an exploded view of a disassemblable far infrared knee-and-foot warming device according to the embodiment of the present invention.
Figure 3:
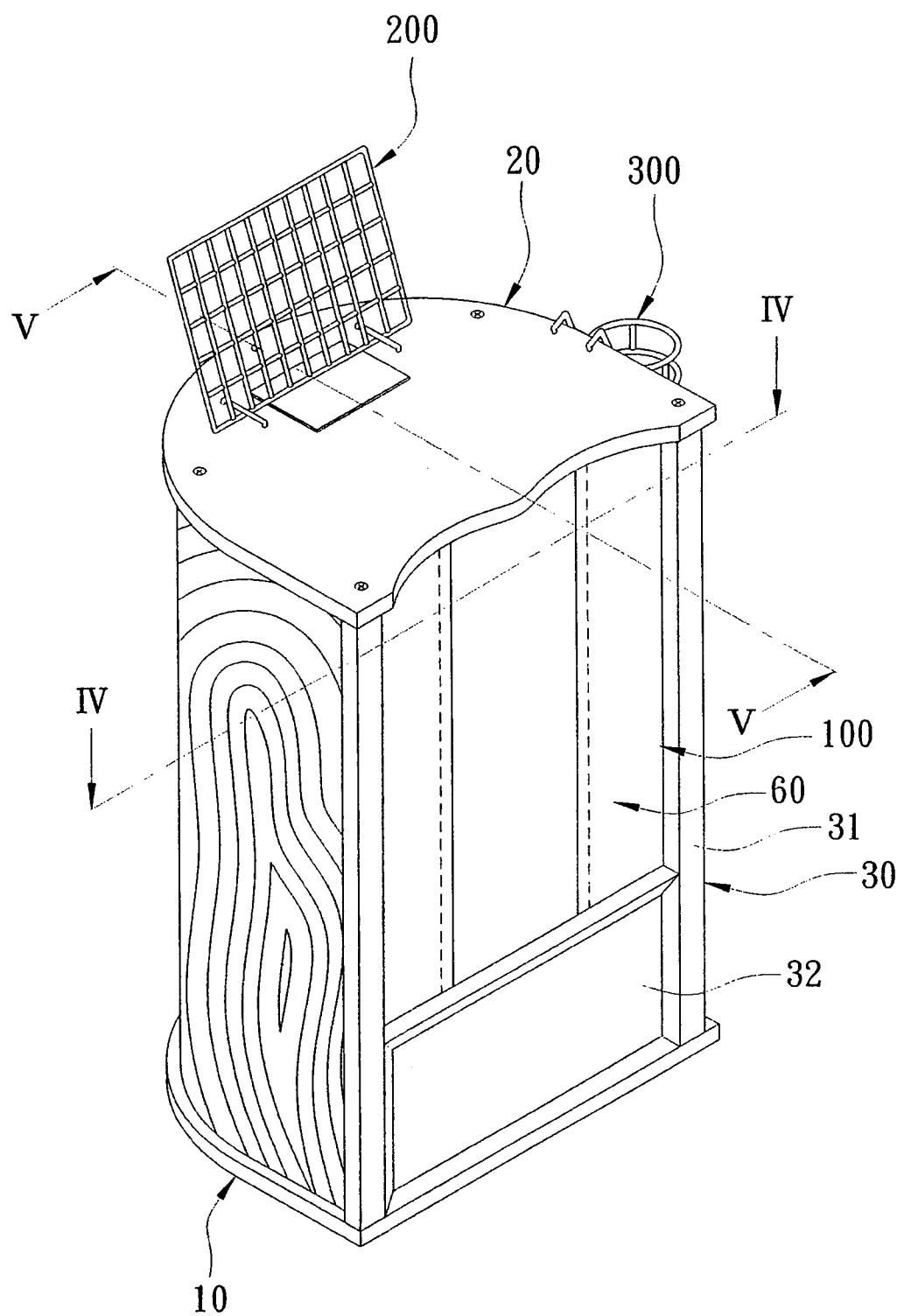
FIG. 3 is a perspective view of the disassemblable far infrared knee-and-foot warming device of FIG. 2.
Figure 5:
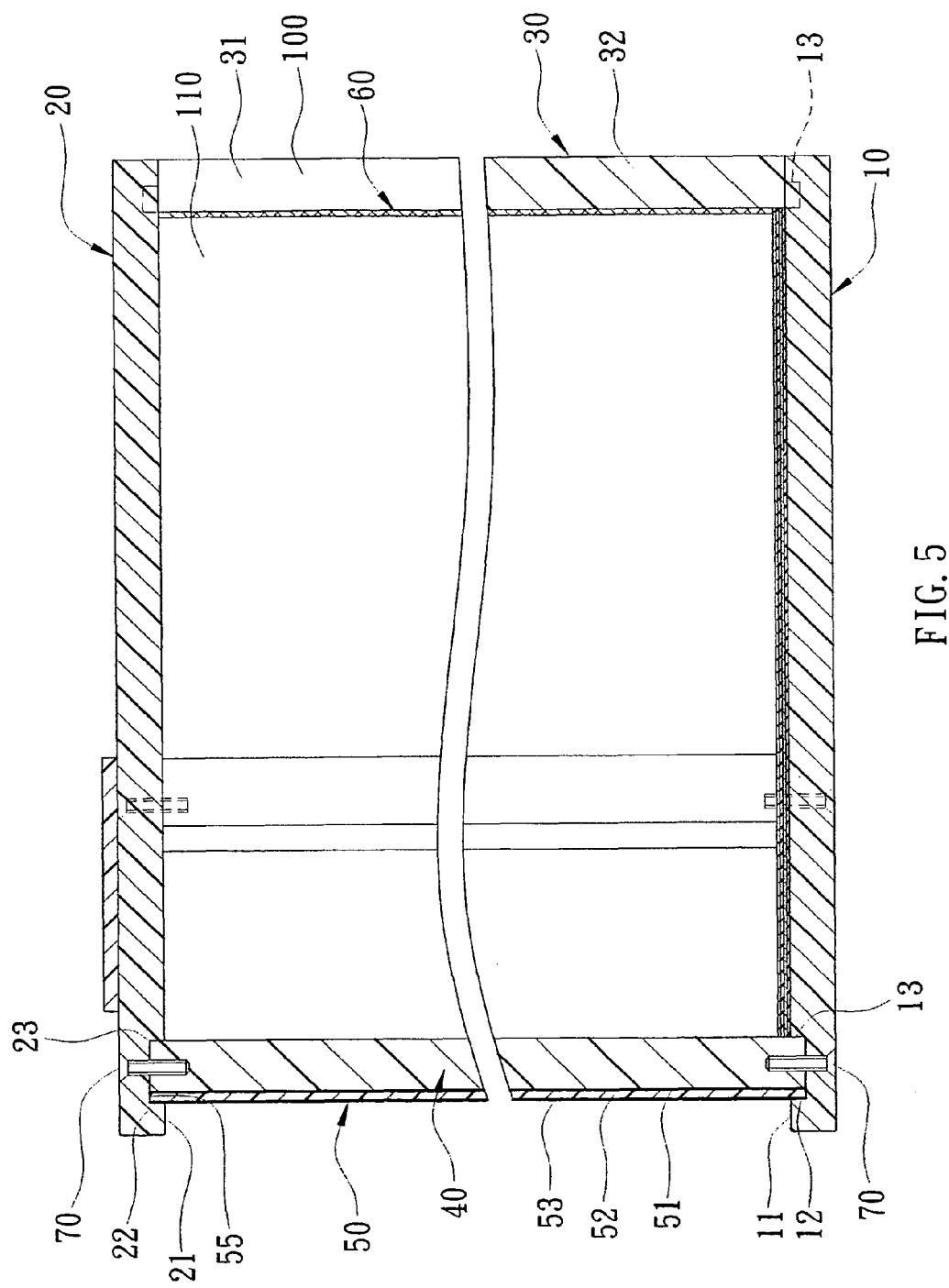
FIG. 5 is another cross-sectional view of the disassemblable far infrared knee-and-foot warming device taken along Line V-V of FIG. 3.

As illustrated in FIG. 2, FIG. 3 and FIG. 5, a disassemblable far infrared knee-and-foot warming device according to one embodiment of the present invention comprises a bottom plate 10, a top plate 20, a front frame 30, a plurality of supporting members 40, a curved plate 50, a plurality of curtain pieces 60, a plurality of screws 70, an auxiliary far infrared heating plate 80 and an opening 100.

The bottom plate 10 with an approximately semicircular outline has an upper surface 11 thereof formed with a lower retaining groove 12 extending along the outline of the bottom plate 10 as an arc and a plurality of lower notches 13 equidistantly distributed inside the lower retaining groove 12 and intercommunicated with the lower retaining groove 12.

The top plate 20 has a lower surface 21 facing the upper surface 11. The lower surface 21 is formed with an upper retaining groove 22 extending along an outline of the top plate 20 as an arc and a plurality of upper notches 23 equidistantly distributed inside the upper retaining groove 22 and intercommunicated with the upper retaining groove 22.

Figure 4:
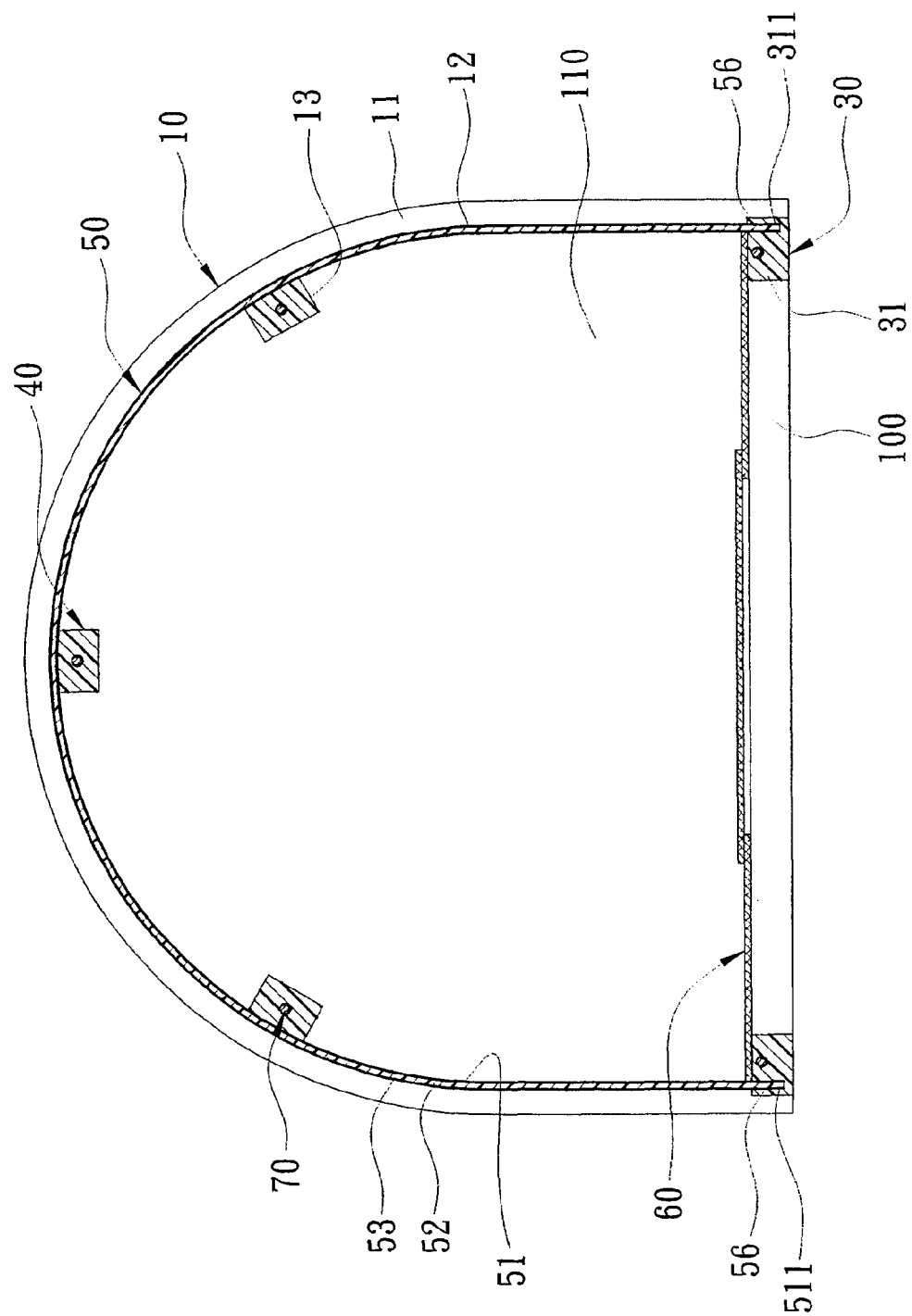
FIG. 4 is a cross-sectional view of the disassemblable far infrared knee-and-foot warming device taken along Line IV-IV of FIG. 3.

The front frame 30 includes two front studs 31 and a parapet 32 connected between the front studs 31. Each of the front studs 31 has two opposite ends retained by the corresponding lower and upper notches 13, 23 while being formed with an axially extending rut 311 (as shown in FIG. 4). Accordingly, the front studs 31, the parapet 32, and the top plate 20 jointly define the opening 100.

Each of the supporting members 40 stands vertically to have two opposite ends thereof retained by the corresponding lower and upper notches 13, 23.

Figure 6:
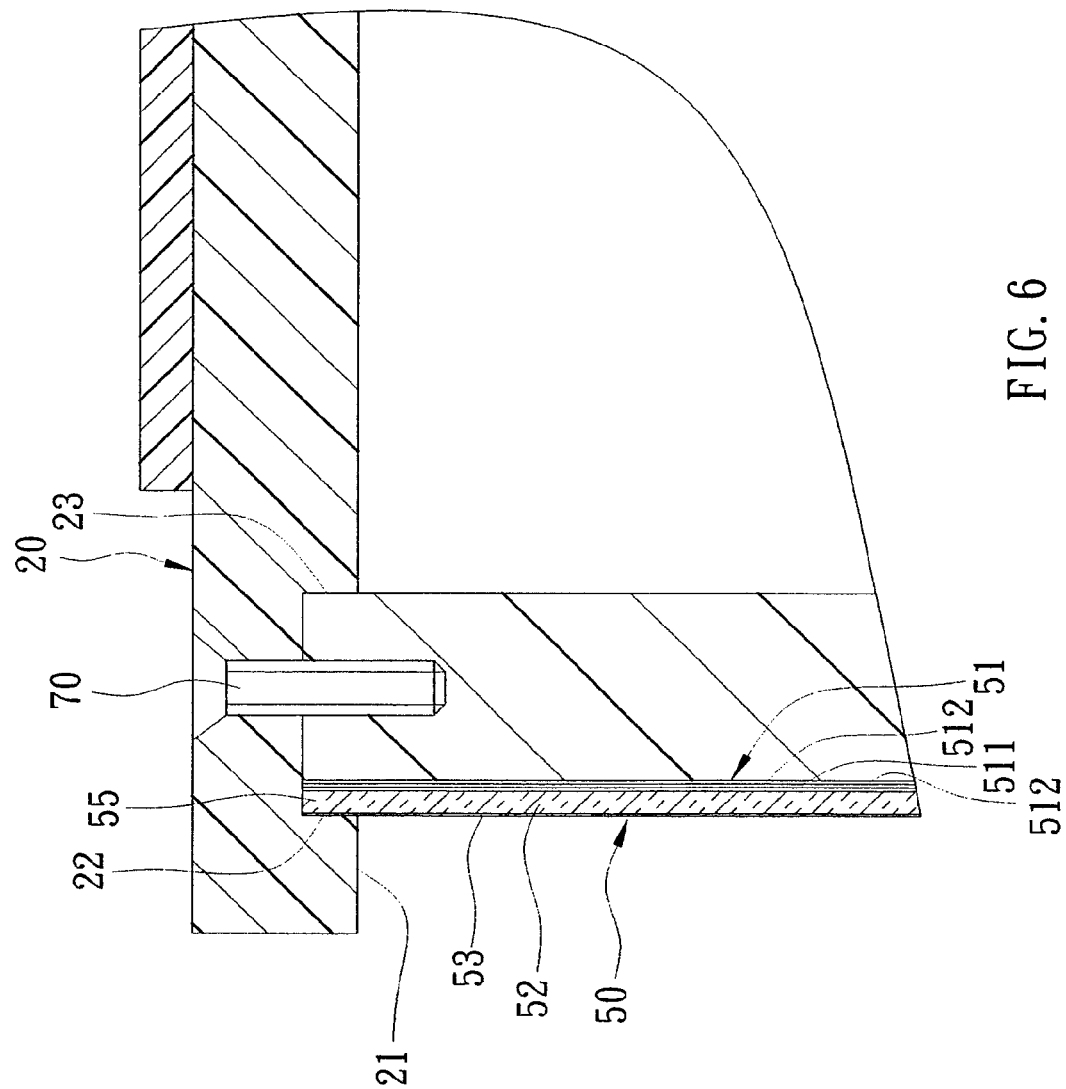
FIG. 6 is an enlarged view of a far infrared heating plate in the disassemblable far infrared knee-and-foot warming device.

The curved plate 50 is, as such, flexible and is equipped with a far infrared heating plate 51, a thermal insulation layer 52 covering outside the far infrared heating plate 51, a pattern layer 53 covering outside the thermal insulation layer 52, a bottom edge 54 to be received in the lower retaining groove 12, a top edge 55 to be received in the upper retaining groove 22, and two opposite lateral edges 56 to be received in the ruts 311 of the front studs 31. Referring to FIG. 6 as well, the far infrared heating plate 51 has two insulation layers 511 and a heating layer 512 sandwiched between the insulation layers 511. The insulation layers 511 are made of glass fiber based epoxy resin, and the heating layer 512 made of graphite serves to generate far infrared thermal energy when supplied with electric power, while the pattern layer 53 is printed with wood grain patterns.

In the present embodiment, the curtain pieces 60 made of elastic fabric and tensioned vertically between the parapet 32 of the front frame 30 and the top plate 20 for closing the opening 100 are flexible and deformable. Each two said adjacent curtain pieces 60 have their adjacent edges overlapping each other, and a user may have his/her lower legs piercing through the overlapped edges.

The screws 70 are screwed from outside of the bottom plate 10 and the top plate 20 so as to fasten the bottom plate 10, the top plate 20, the front frame 30 and the supporting members 40 as a whole.

The auxiliary far infrared heating plate 80 is mounted on the upper surface 11 of the bottom plate 10, while also having two insulation layers 81 and a heating layer 82 sandwiched between the insulation layers 81.

As shown in FIG. 3, FIG. 4 and FIG. 5, when the components are assembled, the bottom and top edges 54, 55 of the curved plate 50 are received in the lower and upper retaining grooves 12, 22 of the lower and top plates 10, 20, and the ends of the supporting members 40 are retained by the lower and upper notches 13, 23 so that the curved plate 50 is retained from rotating and thereby positioned. Meantime, the ends of the front studs 31 of the front frame 30 are also retained by the lower and upper notches 13, 23, allowing the lateral edges 56 of the curved plate 50 to be set in the ruts 311. The screws 70 at this time fastening the bottom plate 10 and the top plate 20 to the supporting members 40 and the front studs 31 fix the assembled device, in which a space 110 is defined. Since the far infrared heating plate 51 is located on the curved plate 50 and the auxiliary far infrared heating plate 80 is preset on the bottom plate 10, in the assembled device, the far infrared heating plate 51 and the auxiliary far infrared heating plate 80 are in the proximity of each other in the space 110.

Referring to FIG. 4 and FIG. 5, in use of the disclosed device, the curtain pieces 60 allow a user to have his/her lower legs piercing through the overlapped edges of the curtain pieces 60 and accessing the space 110. The curtain pieces 60 will then fit the user's legs so that when the far infrared heating plate 51 and the auxiliary far infrared heating plate 80 operate, the generated far infrared thermal energy will be retained in the space 110 to treat the user's knees and feet for the purposes of rehabilitation and/or health care.

The advantages of the present invention can therefore be summarized as below:

1. By operating the screws 70, the bottom plate 10, the top plate 20, the front frame 30, the supporting members 40 and the curved plate 50 can be easily assembled, disassembled and reassembled. In virtue of the lower retaining groove 12 and the lower notches 13 of the bottom plate 10, and the upper retaining groove 22 and the upper notches 23 of the top plate 20, together with the ruts 311 of the front frame 30, the edges of the curved plate 50 can be easily engaged with and disengaged from the bottom plate 10, the top plate 20 and the front frame 30.

2. The supporting members 40 can stably stand between the bottom plate 10 and the top plate 20 to provide the curved plate 50 with required structural strength, thereby securing the overall structure of the device assembled by means of the screws 70.

3. The disclosed device is characterized in being disassemblable, and thus facilitate saving costs related to packaging, storage and transportation while allowing its user to enjoy assembly and disassembly as often as desired.

4. The insulation layers 511, 81 in the far infrared heating plate 51 and the auxiliary far infrared heating plate 80 are made of glass fiber based epoxy resin through a vacuum laminating process, so as to be fully electrically insulating, waterproof, temperature resistant, acid/alkali-resistant, and impact resistant, while being light yet elastic and tough, being contributive to the reduced weight of the overall device. The heating layers 512, 82 are made through screen printing so the manufacturing thereof is very facile.

5. As the components involved in the present invention are made of environmentally friendly materials, the disclosed device advocates preservation of natural resources, and benefits by reduced overall weight (less than 6 kg), thus being practical.

Another aspect of the present invention deserving to be mentioned is that while the opening 100 in the above-described embodiment is formed among the front studs 31, the parapet 32 and the top plate 20, it may be alternatively formed on the top plate 20 (not shown). In addition, the top plate 20 may be further equipped with a book reading holder 200 and a cup holder 300 (as shown in FIG. 3).

The present invention has been described with reference to the preferred embodiments and it is understood that the embodiments are not intended to limit the scope of the present invention. Moreover, as the contents disclosed herein should be readily understood and can be implemented by a person skilled in the art, all equivalent changes or modifications which do not depart from the concept of the present invention should be encompassed by the appended claims.

What is claimed is:

1. A disassemblable far infrared knee-and-foot warming device, comprising:

a bottom plate having an upper surface which is formed with a lower retaining groove extending along an outline of the bottom plate;

a top plate having a lower surface facing the upper surface, wherein the lower surface is formed with an upper retaining groove extending along an outline of the top plate;

a front frame being connected between the bottom plate and the top plate and having two vertically extending ruts;

a curved plate having a far infrared heating plate, a thermal insulation layer covering the far infrared heating plate, a pattern layer covering the thermal insulation layer, a bottom edge to be received in the lower retaining groove, a top edge to be received in the upper retaining groove, and two opposite lateral edges to be received in the ruts, wherein the far infrared heating plate has two insulation layers and a heating layer sandwiched between the insulation layers;

a plurality of screws for fastening the bottom plate, the top plate and the front frame together;

an opening being provided on any one of the top plate and the front frame; and a plurality of supporting members corresponding to the curved plate, wherein the bottom plate further has a plurality of lower notches formed on the upper surface and the top plate further has a plurality of upper notches formed on the lower surface so that opposite ends of each said supporting members are allowed to be retained by corresponding said lower and upper notches.

2. The disassemblable far infrared knee-and-foot warming device of claim 1, wherein the front frame further has two front studs and a parapet connected between the front studs, and the ruts are formed on the front studs, while the front studs of the front frame, the parapet and the top plate jointly define the opening, the disassemblable far infrared knee-and-foot warming device further having a plurality of curtain pieces for closing the opening, wherein the curtain pieces are made of fabric so as to be flexible and deformable, and each two said adjacent curtain pieces have adjacent edges thereof overlapping each other.

3. The disassemblable far infrared knee-and-foot warming device of claim 1, further comprising an auxiliary far infrared heating plate attached to the upper surface of the bottom plate, wherein the auxiliary far infrared heating plate has two insulation layers and a heating layer sandwiched between the insulation layers.

4. The disassemblable far infrared knee-and-foot warming device of claim 3, wherein the insulation layers of the far infrared heating plate and the auxiliary far infrared heating plate are made of glass fiber based epoxy resin, and the heating layers are made of graphite.

* * * * *